United States Patent [19]

Shalaby et al.

[11] 4,388,926

[45] Jun. 21, 1983

[54] HIGH COMPLIANCE MONOFILAMENT SURGICAL SUTURES COMPRISING POLY[ALKYLENE TEREPHTHALATE-CO-(2-ALKENYL OR ALKYL)SUCCINATE]

[75] Inventors: Shalaby W. Shalaby, Lebanon; Edgar Schipper, Cranford, both of N.J.

[73] Assignee: Ethicon, Inc., Somerville, N.J.

[21] Appl. No.: 218,998

[22] Filed: Dec. 22, 1980

[51] Int. Cl.³ .............................................. A61L 17/00
[52] U.S. Cl. .......................................... 128/335.5; 3/1;
128/334 R; 525/437; 528/272
[58] Field of Search ..................... 525/437; 528/272;
128/335.5, 334 R; 3/1

[56] References Cited

U.S. PATENT DOCUMENTS

| 3,542,737 | 11/1970 | Keck et al. | 528/302 |
| 3,883,901 | 5/1975 | Coquard et al. | 528/272 |
| 3,890,279 | 6/1975 | Wolfe et al. | 528/277 |
| 3,891,604 | 6/1975 | Wolfe et al. | 528/291 |
| 4,140,678 | 2/1979 | Shalaby et al. | 525/437 |
| 4,208,511 | 6/1980 | Shalaby et al. | 528/272 |

FOREIGN PATENT DOCUMENTS 1556509 11/1979 United Kingdom .

Primary Examiner—Lucille M. Phynes
Attorney, Agent, or Firm—Nancy A. Bird; Charles J. Metz

[57] ABSTRACT

A high compliance monofilament surgical suture having unique handling and knot tying characteristics, said suture comprising an oriented monofilament of poly[tetramethylene terephthalate-co-(2-alkenyl or alkyl) succinate].

17 Claims, No Drawings

HIGH COMPLIANCE MONOFILAMENT SURGICAL SUTURES COMPRISING POLY[ALKYLENE TEREPHTHALATE-CO-(2-ALKENYL OR ALKYL)SUCCINATE]

BACKGROUND OF THE INVENTION

The present invention relates to new and useful surgical sutures and allied surgical products, and more particularly to strong but limp high compliance, monofilament sutures having unique handling and knot tying characteristics. The novel sutures and surgical products of the present invention comprise a sustantially oriented copolymer made from alkylene terephthalate and 2-alkenyl (or alkyl) succinate sequences.

U.S. Pat. No. 3,890,279 discloses molded articles made from copolymers of this invention having reasonable levels of crystallinity and flexibility as well as good tear strength. Molded articles made of material containing the copolymeric sequence described to this invention are also described in U.S. Pat. No. 3,891,604. From the teaching of these two patents, which relate to molded, practically unoriented articles, little can be predicted concerning the mechanical properties of highly oriented fibers made from these copolymers. Furthermore, U.S. Pat. No. 3,542,737, indicates explicitly that oriented multifilament yarns made from related copolymers, namely those containing ethylene terephthalate and 2-alkenyl succinate (0.5 to 15 mole %) sequences, display almost identical tensile properties when compared with the unmodified rigid yarn made from the high modulus parent homopolymer, polyethylene terephthalate.

Theory and experience in the art of fiber chemistry predict that branching—as present in the polymers described—may prohibit fiber formation and will exert a deleterious effect on the tensile properties of any resulting fibers by the inability of the unoriented branch to contribute to the load bearing capacity of the fiber, and by the steric interference posed by the branch to chain alignment during fiber orientation. It was therefore surprising that strong fibers, in particular strong, compliant "ultralimp" fibers may be formed from poly(tetramethylene terephthalate) copolymers with pendant hydrocarbon chains. Compliance is used in part to denote the reciprocal of modulus.

Many natural and synthetic materials are presently used as surgical sutures. These materials may be used as single filament strands, i.e., monofilament sutures, or as multifilament strands in a braided, twisted or other multifilament construction. Natural materials such as silk, cotton, linen, and the like, do not lend themselves to the fabrication of monofilament sutures and are accordingly generally used in one of the multifilament constructions.

Certain synthetic materials which are extruded in continuous lengths can be used in monofilament form. Common synthetic monofilament sutures include polypropylene, polyethylene and nylon. Such monofilament sutures are preferred by surgeons for many surgical applications due to their inherent smoothness and non-capillarity to body fluids.

Available synthetic monofilament sutures all suffer to greater or lesser degrees from one particular disadvantage, that is relative stiffness. Besides making the material more difficult to handle and use, suture stiffness or low compliance can adversely affect knot tying ability and knot security. It is because of the inherent stiffness of available monofilament sutures that many suture materials are braided or have other multifilament constructions with better handling, flexibility and conformity.

Most monofilament sutures of the prior art are also characterized by a low degree of compliance. This makes knot tying difficult and reduces knot security. In addition, the low compliance and limited ductility prevent the suture from "giving" as a newly sutured wound swells, with the result that the suture may place the wound tissue under greater tension than is desirable, and may even cause some tearing, cutting or necrosis of the tissue.

The problems associated with the use of low compliance sutures in certain applications were recognized in U.S. Pat. No. 3,454,011, where it was proposed to fabricate a surgical suture composed of Spandex polyurethane. Such sutures, however, were too elastic and did not find general acceptance in the medical profession.

Recently issued U.S. Pat. No. 4,224,946 describes a monofilament suture with good flexibility and knot strength, which suture is composed of block polyetheresters which contain (1) a polymeric block of polyalkene esters and (2) a polymeric block of aromatic dicarboxylic acids or cycloaliphatic acids with short chain aliphatic or cycloaliphatic diols.

It is an object of the present invention to provide a novel soft, limp, thermoplastic monofilament suture or ligature of poly[alkylene terephthalate-co(2-alkenyl or alkyl)succinate]. It is a further object of this invention to provide a monofilament suture with a desirable degree of ductility to accommodate changing wound conditions. It is another object of this invention to provide a monofilament suture with the flexibility and knot tying characteristics of a braided suture. It is another object of this invention to provide a new, nonabsorbable suture having a diameter of from about 0.01 to 1.0 mm and possessing unique and desirable physical properties. These and other objects will be made apparent from the ensuing description and claims.

SUMMARY OF THE INVENTION

The general structure of the poly[alkylene terephthalate-co-(2-alkenyl or alkyl)succinate], useful in forming the monofilament sutures of the present invention, may be expressed as follows:

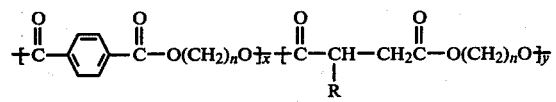

The structure belongs to the copolymer type and x and y can be predicted from the quantities of starting materials used;

"n" is 2 to 6 and preferably is 4, and

"R" is a linear or branched alkyl, or alkenyl (preferred 2-alkenyl) group with a chain length of about 4 to 30 carbon atoms with the preferred range lying between about 12 and 22 carbon atoms.

The composition range in mole percent, useful for fiber formation is about 70–90% poly(alkylene terephthalate) corresponding to 30–10% poly(alkylene alkyl or alkenyl succinate) and preferably is 80–87% and 20–13% respectively. Monofilament sutures of the present invention are characterized by the following combination of physical properties:

Young's modulus—from about 40,000 to 240,000 psi
Tensile strength—at least about 45,000 to 90,000 psi
Knot strength—at least about 30,000 to 60,000 psi
% elongation—at least about 25% to 60%

Sutures possessing the above characteristics may be prepared by melt extrusion, forming a continuous filamentary strand, and drawing the extruded filament to obtain the desired suture properties.

Monofilament sutures having physical properties in accordance with the present invention are particularly useful in many surgical procedures where the suture is used to close a wound which may be subject to later swelling or change in position. The combination of low Young's modulus and high elongation provides the suture with an appreciable degree of ductility and high compliance under low applied force. As a result, the suture is able to "give" to accommodate swelling in the wound area. In addition the ductility and high tensile strength of the suture allow the suture to stretch during knot tie-down so that the knot "snugs down" for improved tying ability and knot security with a more predictable and consistent knot geometry regardless of variations in suture tying technique or tension.

DESCRIPTION OF THE PREFERRED EMBODIMENTS

The polymers useful in the present invention are prepared by the polycondensation of dimethyl terephthalate, an alkyl (or 2-alkenyl) succinic anhydride and a polymethylene diol:

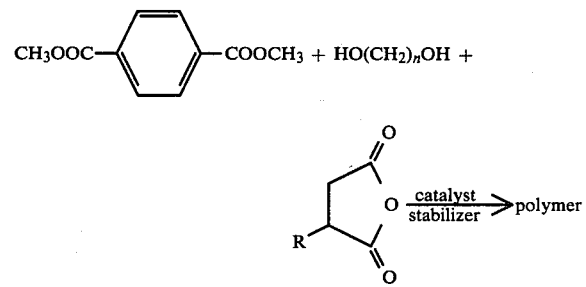

The required diols are commercially available. The substituted succinic anhydrides can be prepared by the "ene" reaction of maleic anhydride and an olefin (preferably a terminal olefin):

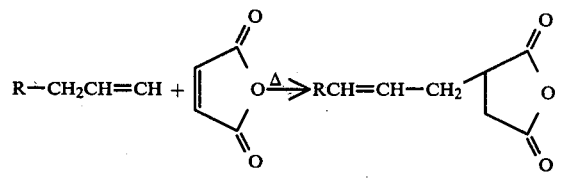

The reaction may be run in the absence or, preferably, in the presence of stabilizers such as hindered phenols, (e.g., Irganox 1098) or secondary aromatic amines, (e.g., Naugard 445). Acetates, oxides and alkoxides of numerous polyvalent metals may be employed as the catalyst such as, for example, zinc acetate, or magnesium acetate in combination with antimony oxide, or zinc acetate together with antimony acetate. However, the preferred catalyst for the polymerization is a mixture of 0.1% (based on total charge weight) tetrabutyl orthotitanate and 0.005% magnesium acetate. If a dyed product is desired, a compatible dye such as, for instance, D&C Green No. 6, can be added to the polymer or monomer mixture in concentrations of up to 0.5% based on expected polymer yield.

The polymerization is run in two stages. In the first stage, run under nitrogen at temperatures ranging from 160° to 250° C., polycondensation via transesterification and esterification occurs, resulting in lower molecular weight polymers and oligomers. These are converted to higher molecular weight materials in the subsequent step run at 240°-255° C., at pressures of less than 1 mm of mercury. The resulting polymers, exhibit inherent viscosities (measured in hexafluoroisopropyl alcohol) of 0.8 to 1.4, crystallinity of about from 20% to 50%. A representative molecular weight determination of one of the polymers by light scattering gave a value of $78 \times 10^3$ daltons. The Tm of the polymers, depending on composition varied from about 180°-210° C. Melt viscosities at suitable extrusion temperatures varied from about $3 \times 10^3$ to about $9 \times 10^3$ poise. A summary of polymer properties is given in Table I.

The polymers are readily extruded in a ram type extruder, as for example an Instron capillary rheometer at 10°-50° C. above the resin Tm, depending on the polymer's molecular weight. The resulting extrudates can be drawn and the total draw ratio may vary from $3\times$ to $7\times$.

The unique oriented fibers exhibit an unexpected combination of properties. For example, strands of about 7-10 mil diameter displayed knot strengths of $35-45 \times 10^3$ psi, straight tensiles in the $50-80 \times 10^3$ psi and a Young's modulus of usually less than $150 \times 10^3$ psi. Percent elongations ranged from 25 to 55.

In summary, the polymers described lend themselves to ready extrusion and drawing to strong and supple fibers which are useful as high compliance "ultralimp" sutures. A list of properties of fibers drawn in a two stage process using either two consecutive heated glycerine baths or a hot shoe followed by a subsequent glycerine bath, is shown in Table II.

The fibers are radiation or ethylene oxide sterilizable, and lose no more than 6% of their strength after implantation for three weeks in a rat's dorsal muscles.

General Polymerization Procedure

The desired amounts of dimethyl terephthalate, a 2-alkenyl succinic anhydride (or an alkylsuccinic anhydride), a 1.3 to 2.0 molar excess of a polymethylene diol and a given stabilizer were placed under nitrogen into a dry reactor fitted with an efficient mechanical stirrer, a gas inlet tube and a takeoff head for distillation. The system was heated under nitrogen to 160° C. and stirring was begun. To the homogeneous stirred reaction mixture the required amount of catalyst was added. The mixture was then stirred and heated under nitrogen for given time periods at 190° C. (2-4 hours) and 220° C. (1-3 hours). The temperature was subsequently raised to 250°-255° C. and over a period of 0.4-0.7 hours, the pressure was reduced in the system to about 1 mm/Hg (preferably 0.05 mm to 0.1 mm). Stirring and heating under the above conditions was continued to complete the polymerization. The endpoint was determined by either (a) estimating visually the attainment of maximum melt viscosity, (b) measuring inherent viscosity or melt indices of samples removed from the reaction vessel at intermediate time periods, or (c) using a calibrated torquemeter (attached to the stirrer of the reactor).

At the end of the polymerization cycle the molten polymer was extruded and pelletized (or slow cooled in the glass reactor, isolated and ground in a mill). The polymer was dried at 80°–110° C. for 8–16 hours under reduced pressure prior to extrusion. One alternate method of polymerization is set forth in U.S. Pat. No. 3,890,279.

General Extrusion Procedure

Extrusion using the Instron Capillary Rheometer produced an extrudate which upon drawing (3× to 7× ratio) yielded fibers in the 7–10 mil diameter range (size 3/0 to 4/0 sutures). The polymers were packed in the extrusion chamber, heated to about 130° C., and extruded through a 40 mil die after a dwell time of 9 to 13 minutes. The ram speed was 2 cm/minute. While extrusion temperatures depend both on the polymer Tm and on the melt viscosity of the material at a given temperature, extrusion at temperatures of 10°–50° C. above the Tm was usually satisfactory. The extrudate was taken up at a speed of about 18 feet per minute.

General Drawing Procedure

The extrudate (diameter range, 19–22 mils) was passed through rollers at an input speed of four feet per minute and then over a hot shoe or into a heated draw bath of glycerine. The temperatures of the hot shoe or draw bath varied from about 50° C. to 95° C. The draw ratio in this first stage of stretching varied from 3× to 6×. The drawn fibers were then placed over another set of rollers into a glycerine bath (second stage) kept at temperatures ranging from about 60° C. to 100° C. Draw ratios of up to 2× were applied but usually only a slight amount of fiber extension (1.25×) was found desirable at this stage. Finally, the fiber was passed through a water wash, dried and taken up on a spool.

EXAMPLE I

The following materials were reacted under dry nitrogen at 160° C. for several minutes:

49.6 g. dimethyl terephthalate (0.2557 M)
24.0 g. 2-docosenyl succinic anhydride (0.0590 M)
41.2 g. 1,4-butanediol (0.4578 M)
0.8 g. 4,4'-bis($\alpha,\alpha$-dimethylbenzyl)diphenyl amine When the reaction mixture liquified agitation was begun, the catalyst (1.0 ml) consisting of 0.1% tetrabutyl orthotitanate and 0.005% magnesium acetate (percentages based on total charge weight) dissolved in a mixture of methanol and butanol was added. The reaction mixture was then heated under nitrogen at 190° C. for 3 hours and at 220° C. for another 2 hours. As the methanol distillation ceased, the reaction temperature was increased to about 250° C., and the pressure in the reactor was reduced to about 0.1 mm. The mixture was heated at this pressure and at about 250° C. for up to 11 hours. The hot viscous mass was blanketed with an atmosphere of nitrogen and allowed to cool to room temperature. The polymer was isolated, ground and dried (under reduced pressure for 8 hours at 80° C.). Properties of the polymer and others prepared under similar reaction conditions are shown in Table I.

EXAMPLE II

Ten grams of the copolymer described in Example I were packed at about 130° C. into the extrusion chamber of an Instron Rheometer and, after 10 minutes of dwell time, the sample was extruded at a ram speed of 2 cm/minute, a shear rate of 212.6 sec$^{-1}$ and a temperature of 205° C. The resulting melt viscosity was found to be 3438 poise. The takeup speed of the extrudate was 18 ft/minute and the extrudate was quenched in ice water. The diameter of extrudate was 21.0–22.0 mils.

The extrudate was drawn at 5× through a glycerine bath held at a temperature of 82° C. and at 1.25× through a second glycerine bath heated to 70° C. The resulting fiber was washed in a water bath (room temperature) to remove the glycerine and taken up on a spool. The draw tension for both the first and second drawing stage was 230 g and the total draw ratio was 6.25×. Tensile data for fiber obtained by this and other extrusion and draw experiments are shown in Table II.

EXAMPLE III

Fibers prepared from polymer No. 3 (Table I) were strung under a tension of 50 g. on an annealing rack adjustable for length. The adjustable bar was lowered ca. 10% to allow the fibers to relax freely. After 16 hours the adjustable bar was raised to a height which was sufficient to straighten the fibers without imparting any tension (0% relaxation). The fibers were then heated for one hour of heating at 110° C., cooled and cut off the annealing rack. Fibers annealed in this manner, allowed to shrink freely at 60° C. for 2.5 hours were found to shrink 1.8% as opposed to 17.8% for identical unannealed strands.

EXAMPLE IV

Polymer compositions containing 70 weight percent of tetramethylene terephthalate and 30 weight percent of tetramethylene 2-alkenyl succinate (or alkyl succinate) sequences were formed, extruded and drawn to yield fibers having the properties shown in Table II.

Poly[tetramethylene terephthalate co(2-alkenyl or alkyl)succinate] may be spun as multifilament yarn and woven or knitted to form sponges or gauze, or used in conjunction with other compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged kidney, liver and other abdominal organs, protecting damaged surface areas such as abrasions, particularly major abrasions, or areas where the skin and underlying tissues are damaged or surgically removed.

In more detail, the medical uses of poly[alkylene terephthalate co(2-alkenyl or alkyl)succinate] include, but are not necessarily limited to:

1. Solid products, molded or machined
   a. orthopedic pins, clamps, screws and plates
   b. clips
   c. staples
   d. hooks, buttons, and snaps
   e. bone substitutes (e.g., mandible prosthesis)
   f. needles
   g. intrauterine devices h. draining or testing tubes or capillaries
i. surgical instruments
j. vascular implants or supports
k. vertebal dics
l. Extracorporeal tubing for kidney and heart-lung machines
2. Fibrillar products, knitted, woven, or nonwoven including velours
   a. burn dressings
   b. hernia patches
   c. absorbent paper or swabs
   d. medicated dressings
e. facial substitutes
f. gauze, fabric, sheet, felt or sponge for liver hemostasis
g. gauze bandages
h. dental packs, and In combination with other components
1. Solid products, molded or machined
   a. reinforced bone pins, needles, etc.
2. Fibrillar products
   a. arterial graft or substitutes
   b. bandages for skin surfaces
   c. burn dressings (in combination with polymeric films)

TABLE I

SYNTHESIS AND PROPERTIES OF POLY(TETRAMETHYLENE TEREPHTHALATE-CO-2-ALKYLENESUCCINATE) AND POLY(TETRAMETHYLENE TEREPHTHALATE-CO-ALKYLSUCCINATE) POLYMERS

| Sample No. | Succinic Anhydride Used in Polymerization | Monomer Ratio* S/T (moles) | Stabilizer** % | Stabilizer** Type | % D & C Green #6 | Polymerization Reaction Scheme °C. | Polymerization Reaction Scheme p(mm) | Polymerization Reaction Scheme hrs. | $\eta_{inh}$ 25° C. (HFIP) | M.p. °C. (microscopy) | % Crystall. (X-ray) |
|---|---|---|---|---|---|---|---|---|---|---|---|
| 1 | 2-docosenyl | 19/81 | 1.0 | Naugard 445 | 0 | See Example 1 | | | 0.88 | 185–190 | 28 |
| 2 | 2-docosenyl | 17/83 | 1.0 | Naugard 445 | 0 | 160 | atm.N$_2$ | 0.2 | 1.00 | 188–192 | 39 |
| | | | | | | 190 | " | 3.0 | | | |
| | | | | | | 220 | " | 3.0 | | | |
| | | | | | | 255 | 0.08 | 11.0 | | | |
| 3 | 2-docosenyl | 17/83 | 1.0 | Naugard 445 | 0.3 | 160 | atm.N$_2$ | 0.2 | 0.90 | 188–192 | 35 |
| | | | | | | 190 | " | 3.5 | | | |
| | | | | | | 220 | " | 2.0 | | | |
| | | | | | | 250 | 0.08 | 14.0 | | | |
| 4 | 2-docosenyl | 13/87 | 1.0 | Naugard 445 | 0 | 160 | atm.N$_2$ | 0.2 | 1.03 | 197–200 | 40 |
| | | | | | | 190 | " | 3.0 | | | |
| | | | | | | 250 | " | 0.5 | | | |
| | | | | | | 250 | 0.05 | 3.5 | | | |
| 5 | 2-docosenyl | 13/87 | 0 | None | 0 | 160 | atm.N$_2$ | 0.2 | 0.71 | 197–199 | 40 |
| | | | | | | 220 | " | 1.5 | | | |
| | | | | | | 250 | " | 0.75 | | | |
| | | | | | | 250 | 0.05 | 5.5 | | | |
| 6 | 2-docosenyl | 13/87 | 0.25 | Irganox 1098 | 0 | 160 | atm.N$_2$ | 0.2 | 0.77 | 197–198 | 41 |
| | | | | | | 190 | " | 3.0 | | | |
| | | | | | | 250 | " | 0.5 | | | |
| | | | | | | 250 | 0.05 | 1.5 | | | |
| 7 | 2-docosenyl | 11/89 | 1.0 | Naugard 445 | 0 | 160 | atm.N$_2$ | 0.2 | 1.15 | 199–203 | 34 |
| | | | | | | 190 | " | 3.0 | | | |
| | | | | | | 220 | " | 2.0 | | | |
| | | | | | | 255 | 0.08 | 3.0 | | | |
| 8 | docosanyl | 16/84 | 1.0 | Naugard 445 | 0 | 160 | atm.N$_2$ | 0.2 | 0.79 | 190–194 | 36 |
| | | | | | | 190 | " | 3.5 | | | |
| | | | | | | 220 | " | 2.0 | | | |
| | | | | | | 250 | 0.08 | 14.0 | | | |
| 9 | 2-octadecenyl | 18/82 | 1.0 | Naugard 445 | 0.3 | 160 | atm.N$_2$ | 0.2 | 1.00 | 190–191 | 30 |
| | | | | | | 190 | " | 3.0 | | | |
| | | | | | | 220 | " | 2.0 | | | |
| | | | | | | 250 | " | 1.0 | | | |
| | | | | | | 250 | 0.05 | 6.25 | | | |
| 10 | 2-octadecenyl | 15/85 | 1.0 | Naugard 445 | 0.3 | 160 | atm.N$_2$ | 0.2 | 1.06 | 195–198 | 28 |
| | | | | | | 190 | " | 3.0 | | | |
| | | | | | | 220 | " | 2.0 | | | |
| | | | | | | 250 | " | 1.0 | | | |
| | | | | | | 250 | 0.05 | 6.0 | | | |
| 11 | 2-hexadecenyl | 19/81 | 1.0 | Naugard 445 | 0.3 | 160 | atm.N$_2$ | 0.2 | 1.13 | 185–187 | 26 |
| | | | | | | 190 | " | 3.0 | | | |
| | | | | | | 220 | " | 2.0 | | | |
| | | | | | | 250 | 0.08 | 7.0 | | | |
| 12 | hexadecyl | 19/81 | 1.0 | Naugard 445 | 0.3 | 160 | atm.N$_2$ | 0.2 | 1.16 | 181–183 | 22 |
| | | | | | | 190 | " | 3.0 | | | |
| | | | | | | 220 | " | 2.0 | | | |
| | | | | | | 250 | 0.05 | 6.0 | | | |
| 13 | 2-tetradecenyl | 20/80 | 1.0 | Naugard 445 | 0.3 | 160 | atm.N$_2$ | 0.2 | 1.57 | 195–198 | 28 |
| | | | | | | 190 | " | 3.0 | | | |
| | | | | | | 220 | " | 2.0 | | | |
| | | | | | | 250 | " | 1.0 | | | |
| | | | | | | 250 | 0.08 | 5.25 | | | |
| 14 | 2-dodecenyl | 22/78 | 1.0 | Naugard 445 | 0.3 | 160 | atm.N$_2$ | 0.2 | 1.26 | 185–186 | 28 |
| | | | | | | 190 | " | 3.0 | | | |
| | | | | | | 220 | " | 2.0 | | | |
| | | | | | | 250 | 0.05 | 7.0 | | | |
| 15 | 2-dodecenyl | 18/82 | 1.0 | Naugard 445 | 0.3 | 160 | atm.N$_2$ | 0.2 | 1.07 | 189–191 | 28 |
| | | | | | | 190 | " | 3.0 | | | |
| | | | | | | 220 | " | 2.0 | | | |

TABLE I-continued

SYNTHESIS AND PROPERTIES OF POLY(TETRAMETHYLENE TEREPHTHALATE-CO-2-ALKYLENESUCCINATE)
AND POLY(TETRAMETHYLENE TEREPHTHALATE-CO-ALKYLSUCCINATE) POLYMERS

| Sample No. | Succinic Anhydride Used in Polymerization | Monomer Ratio* S/T (moles) | Stabilizer** % | Stabilizer** Type | % D & C Green #6 | Polymerization Reaction Scheme °C. | Polymerization Reaction Scheme p(mm) | Polymerization Reaction Scheme hrs. | $\eta_{inh}$ 25° C. (HFIP) | M.p. °C. (micros- copy) | % Crystall. (X-ray) |
|---|---|---|---|---|---|---|---|---|---|---|---|
| 16 | dodecyl | 21/79 | 1.0 | Naugard 445 | 0.3 | 250 | 0.05 | 7.0 | 1.11 | 181-183 | 29 |
|  |  |  |  |  |  | 160 | atm.N$_2$ | 0.2 |  |  |  |
|  |  |  |  |  |  | 190 | " | 3.0 |  |  |  |
|  |  |  |  |  |  | 220 | " | 2.0 |  |  |  |
|  |  |  |  |  |  | 250 | " | 1.0 |  |  |  |
|  |  |  |  |  |  | 250 | 0.05 | 4.5 |  |  |  |

*S = substituted succinic anhydride;
T = dimethylterephthalate
**Naugard 445: 4,4'Bis(α,α-dimethylbenzyl)diphenyl amine
Irganox 1098: N,N'—hexamethylene bis(3,5-ditert-butyl-4-hydroxy hydrocinnamide)

TABLE II

EXTRUSION AND DRAWING CONDITIONS AND ULTIMATE TENSILE PROPERTIES
FOR FIBER DERIVED FROM POLY(TETRAMETHYLENE TEREPHTHALATE-CO-2-
ALKYLENESUCCINATE) AND POLY(TETRAMETHYLENE TEREPHTHALATE-CO-ALKYL-
SUCCINATE) POLYMERS

| Polymer Sample No. | Extrusion Conditions T °C. | Extrusion Conditions $\eta_{app}$ (poise) | Drawing Conditions Ratio 1st Stage | Drawing Conditions Ratio 2nd Stage | Drawing Conditions T °C. 1st | Drawing Conditions T °C. 2nd | Dia. (mil) | Tensile Properties Knot psi × $10^{-3}$ | Tensile Properties Straight psi × $10^{-3}$ | Tensile Properties % Elongation | Tensile Properties Y.M. psi × $10^{-3}$ |
|---|---|---|---|---|---|---|---|---|---|---|---|
| 1 | 205 | 3438 | 5x | 1.25x | 82 | 70 | 9.3 | 34.6 | 52.6 | 45 | 69.3 |
| 2 | 200 | 8810 | 5x | 1.25x | 82 | 69 | 8.5 | 41.8 | 65.2 | 41 | 80.8 |
| 3 | 210 | 3223 | 5x | 1.4x | 82 | 92 | 8.3 | 34.0 | 73.7 | 40 | 85.6 |
| 4 | 210 | 6984 | 6x | — | 79 | — | 9.1 | 41.7 | 75.5 | 35 | 128.1 |
| 5 | 205 | 2149 | 6x | 1.08x | 79 | 65 | 8.7 | 33.0 | 41.4 | 35 | 154.6 |
| 6 | 210 | 2041 | 6.75x | 1x | 79 | 69 | 8.3 | 39.6 | 68.2 | 33 | 176.8 |
| 7 | 220 | 8165 | 6x | 1.04x | 82 | 70 | 9.2 | 47.0 | 84.5 | 25 | 217.7 |
| 8 | 200 | 3492 | 6x | 1.25x | 77 | 65 | 8.2 | 36.9 | 55.9 | 33 | 148.8 |
| 9 | 210 | 4674 | 5x | 1.2x | 91 | 95 | 8.8 | 35.2 | 72.0 | 39 | 73.3 |
| 10 | 220 | 4566 | 5x | 1.2x | 88 | 70 | 8.9 | 41.6 | 69.1 | 33 | 147.3 |
| 11 | 215 | 5372 | 5x | 1.2x | 91 | 95 | 8.6 | 35.3 | 76.2 | 46 | 58.3 |
| 12 | 215 | 6017 | 5x | 1.2x | 52 | 70 | 8.9 | 40.5 | 71.9 | 50 | 60.4 |
| 13 | 185 | 3223 | 5x | 1.4x | 90 | 95 | 8.2 | 30.7 | 49.8 | 55 | 39.3 |
| 14 | 220 | 6446 | 5x | 1.2x | 91 | 95 | 8.8 | 39.3 | 74.3 | 41 | 96.5 |
| 15 | 220 | 4351 | 5x | 1.2x | 82 | 75 | 9.2 | 40.5 | 66.8 | 36 | 105.1 |
| 16 | 200 | 4674 | 5x | 1.3x | 91 | 95 | 8.7 | 37.3 | 68.8 | 49 | 54.4 |

We claim:

1. A drawn and highly oriented thermoplastic surgical filament comprising a copolymer consisting essentially of a multiplicity of recurring polyalkylene terephthalate and polyalkylene alkyl or alkenyl succinate units having the following general formula:

$$\vphantom{X} \text{(I)} \quad {+}\overset{O}{\overset{\|}{C}}{-}\hspace{-2pt}\bigcirc\hspace{-2pt}{-}\overset{O}{\overset{\|}{C}}{-}O(CH_2)_nO{\vphantom{]}}_{\overline{x}}\ {+}\overset{O}{\overset{\|}{C}}{-}\underset{R}{\overset{}{CH}}{-}CH_2\overset{O}{\overset{\|}{C}}{-}O(CH_2)_nO{\vphantom{]}}_{\overline{y}}$$

wherein n is 2 to 6, R is a linear or branched alkyl or alkenyl radical with a chain length of about 4 to 30 carbon atoms and x and y are integers such that the polyalkylene terephthalate units comprise 70 to 90 mole percent of the copolymer.

2. A filament of claim 1 having a surgical needle attached to at least one end and useful as a surgical suture.

3. A filament of claim 2 in a sterile condition.

4. A filament of claim 1 wherein R is dodecyl or 2-dodecenyl.

5. A filament of claim 1 wherein R is tetradecyl or 2-tetradecenyl.

6. A filament of claim 1 wherein R is 2-hexadecenyl or hexadecyl.

7. A filament of claim 1 wherein R is octadecyl or 2-octadecenyl.

8. A filament of claim 1 wherein R has a chain length of about 12 to 18 carbon atoms.

9. A filament of claim 1 wherein the polyalkylene units comprise about 80 to 87 mole percent of the copolymer.

10. A filament of claim 1 characterized by the following properties:

Tensile strength—at least 45,000 to 90,000 psi
Knot strength—at least 30,000 to 60,000 psi
Young's modulus—at least 40,000 to 240,000 psi
% elongation—at least about 25% to 60%.

11. A woven or knitted surgical fabric comprised of filaments of claims 1 or 10.

12. A fabric of claim 7 in a seamless tubular construction.

13. A method of closing a wound by approximating and securing the wound tissue with a surgical fiber of claims 1 or 10.

14. A method of closing a wound by approximating and securing the wood tissue with a surgical fiber of claims 1 or 10.

15. A method of closing a wound by approximating and securing the wound tissue with a surgical fiber of claims 1 or 10.

16. A solid surgical aid molded or machined of an oriented thermoplastic copolymer consisting essentially of a multiplicity of recurring polyalkylene terephthalate and polyalkylene alkyl or alkenyl succinate units having the following general formula:

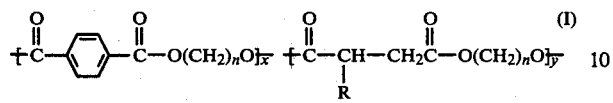

where n is 2 to 6, R is a linear or branched alkyl or alkenyl radical with a chain length of about 4 to 30 carbon atoms and x and y are integers such that the polyalkylene terephthalate units comprise about 70 to 90 mole percent of the copolymer.

17. A fibrillar surgical aid comprising knitted woven or nonwoven oriented fibers of a thermoplastic copolymer consisting essentially of a multiplicity of recurring polyalkylene terephthalate and polyalkylene alkyl or alkenyl succinate units having the following general formula:

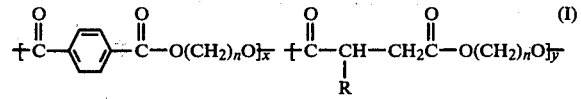

where n is 2 to 6, R is a linear or branched alkyl or alkenyl radical with a chain length of about 4 to 30 carbon atoms and x and y are integers such that the polyalkylene terephthalate units comprise about 70 to 90 mole percent of the copolymer.

* * * * *